(12) United States Patent
Ishizuka et al.

(10) Patent No.: US 11,224,852 B2
(45) Date of Patent: Jan. 18, 2022

(54) CHEMICAL REACTION APPARATUS AND CHEMICAL REACTION METHOD

(75) Inventors: Akinori Ishizuka, Osaka (JP); Iwao Yoshino, Osaka (JP); Kunitaka Momota, Osaka (JP)

(73) Assignee: MICROWAVE CHEMICAL CO., LTD., Osaka (JP)

( * ) Notice: Subject to any disclaimer, the term of this patent is extended or adjusted under 35 U.S.C. 154(b) by 661 days.

(21) Appl. No.: 14/123,174

(22) PCT Filed: Jun. 29, 2011

(86) PCT No.: PCT/JP2011/064965
§ 371 (c)(1),
(2), (4) Date: Nov. 29, 2013

(87) PCT Pub. No.: WO2013/001629
PCT Pub. Date: Jan. 3, 2013

(65) Prior Publication Data
US 2014/0121395 A1 May 1, 2014

(51) Int. Cl.
*B01J 19/12* (2006.01)
*H05B 6/80* (2006.01)
(Continued)

(52) U.S. Cl.
CPC ......... *B01J 19/126* (2013.01); *B01J 19/0013* (2013.01); *B01J 19/0066* (2013.01);
(Continued)

(58) Field of Classification Search
CPC .. B01J 19/126; B01J 19/0013; B01J 19/0066; B01J 19/1862; B01J 2219/00006; B01J 2219/00063; B01J 2219/00141; B01J 2219/00166; B01J 2219/00182; B01J 2219/002; B01J 2219/00238;
(Continued)

(56) References Cited

U.S. PATENT DOCUMENTS

| 3,170,769 A * | 2/1965 | Stiles | B01D 11/0457 |
| | | | 422/227 |
| 3,463,627 A | 8/1969 | Le Blanc | |

(Continued)

FOREIGN PATENT DOCUMENTS

| CN | 1729049 | 2/2006 |
| CN | 101954266 A | 1/2011 |

(Continued)

OTHER PUBLICATIONS

Supplementary European Search Report dated Feb. 26, 2015 which issued during prosecution of EP Application No. 11868832.4.
(Continued)

*Primary Examiner* — Xiuyu Tai
(74) *Attorney, Agent, or Firm* — Troutman Pepper Hamilton Sanders LLP

(57) ABSTRACT

A chemical reaction apparatus includes a horizontal flow-type reactor in which a content horizontally flows with an unfilled space being provided thereabove, a microwave generator that generates microwaves, and at least one waveguide that transmits the microwaves generated by the microwave generator to the unfilled space in the reactor.

25 Claims, 13 Drawing Sheets

(51) Int. Cl.
- *B01J 19/00* (2006.01)
- *H05B 6/70* (2006.01)
- *B01J 19/18* (2006.01)
- *C11C 3/00* (2006.01)
- *C07C 67/08* (2006.01)

(52) U.S. Cl.
CPC ......... *B01J 19/1862* (2013.01); *C07C 67/08* (2013.01); *C11C 3/003* (2013.01); *H05B 6/707* (2013.01); *H05B 6/806* (2013.01); *B01J 2219/002* (2013.01); *B01J 2219/00006* (2013.01); *B01J 2219/00063* (2013.01); *B01J 2219/00141* (2013.01); *B01J 2219/00166* (2013.01); *B01J 2219/00182* (2013.01); *B01J 2219/00238* (2013.01); *B01J 2219/0892* (2013.01); *B01J 2219/1218* (2013.01); *B01J 2219/1266* (2013.01); *B01J 2219/1272* (2013.01); *B01J 2219/1275* (2013.01); *B01J 2219/1284* (2013.01); *B01J 2219/1296* (2013.01)

(58) Field of Classification Search
CPC ........ B01J 2219/0892; B01J 2219/1218; B01J 2219/1266; B01J 2219/1272; B01J 2219/1275; B01J 2219/1284; B01J 2219/1296; C07C 67/08; C11C 3/003; H05B 6/707; H05B 6/806; H05B 6/78; H05B 6/784; C03B 5/182; C03B 5/023; C03B 5/20; F27B 3/20; F27B 3/19; F27B 3/18; F27D 99/0006; F27D 19/00; F27D 2099/0028; B28C 7/0418; B28C 7/0422; B01F 13/1013; B01F 15/00207; B01F 15/00233; B01F 13/1016; B01F 7/16; E21B 21/062; G05D 21/02

See application file for complete search history.

(56) References Cited

U.S. PATENT DOCUMENTS

| | | | |
|---|---|---|---|
| 4,269,805 A | 5/1981 | Schoengen et al. | |
| 4,279,722 A | 7/1981 | Kirkbride | |
| 4,718,358 A * | 1/1988 | Nomi | F23G 5/085 |
| | | | 110/250 |
| 4,844,838 A | 7/1989 | Ohtsuka et al. | |
| 5,393,320 A | 2/1995 | Gomez | |
| 5,458,897 A | 10/1995 | Pare | |
| 5,822,879 A | 10/1998 | Vincent et al. | |
| 6,484,539 B1 * | 11/2002 | Nordine | C03B 37/02 |
| | | | 428/364 |
| 6,723,999 B2 | 4/2004 | Holl | |
| 7,087,220 B2 | 8/2006 | Li | |
| 7,348,182 B2 | 3/2008 | Martin | |
| 8,328,997 B2 | 12/2012 | Charlier De Chily et al. | |
| 10,464,040 B2 | 11/2019 | Ishizuka et al. | |
| 2003/0066792 A1 * | 4/2003 | Xia | B01D 24/30 |
| | | | 210/189 |
| 2004/0056026 A1 | 3/2004 | Jakes et al. | |
| 2006/0228088 A1 | 10/2006 | Charlier De Chily et al. | |
| 2006/0237300 A1 | 10/2006 | Stroder • et al. | |
| 2007/0295717 A1 | 12/2007 | Horikawa et al. | |
| 2010/0172202 A1 | 6/2010 | Borgstadt | |
| 2010/0212492 A1 | 8/2010 | Miotto et al. | |
| 2011/0263843 A1 | 10/2011 | Watanabe et al. | |
| 2013/0102804 A1 | 4/2013 | Charlier De Chily et al. | |

FOREIGN PATENT DOCUMENTS

| | | |
|---|---|---|
| EP | 0626871 B1 | 4/1997 |
| EP | 2727647 A1 | 5/2014 |
| JP | S51-041679 A | 4/1976 |
| JP | S 52-35350 | 3/1977 |
| JP | S59-004431 A | 1/1984 |
| JP | S63-198899 A | 8/1988 |
| JP | S63-285121 A | 11/1988 |
| JP | H 0266497 | 3/1990 |
| JP | H03-109296 U | 11/1991 |
| JP | H 06-041545 | 2/1994 |
| JP | H07-258117 A | 10/1995 |
| JP | H07309433 A | 11/1995 |
| JP | H08-501016 A | 2/1996 |
| JP | H08242783 A | 9/1996 |
| JP | H09285282 A | 11/1997 |
| JP | H 1050470 | 2/1998 |
| JP | 2001009009 A | 1/2001 |
| JP | 2002-079078 A | 3/2002 |
| JP | 2004-201967 A | 7/2004 |
| JP | 2004-216200 A | 8/2004 |
| JP | 2006-511775 | 4/2006 |
| JP | 2006-512554 A | 4/2006 |
| JP | 2006512554 A | 4/2006 |
| JP | 20060512554 | 4/2006 |
| JP | 2006-516008 A | 6/2006 |
| JP | 2006-257304 A | 9/2006 |
| JP | 2007-000774 A | 1/2007 |
| JP | 2007-059317 A | 3/2007 |
| JP | 2007-059318 A | 3/2007 |
| JP | 2007-222696 A | 9/2007 |
| JP | 2007-307440 | 11/2007 |
| JP | 2007-326013 | 12/2007 |
| JP | 2008501016 | 1/2008 |
| JP | 2008-302281 | * 12/2008 |
| JP | 2008-302281 A | 12/2008 |
| JP | 2009-183198 | 8/2009 |
| JP | 2010-111865 | 5/2010 |
| JP | 2010-184230 | 8/2010 |
| JP | 2011-235262 | 11/2011 |
| JP | 2011-235263 | 11/2011 |
| WO | 9314821 | 8/1993 |
| WO | WO1993/014821 A1 | 8/1993 |
| WO | 2004056468 A1 | 7/2004 |
| WO | 2004056471 A1 | 7/2004 |
| WO | WO2004/056471 A1 | 7/2004 |
| WO | WO2004066683 A1 | 8/2004 |
| WO | WO2005/102510 A1 | 11/2005 |
| WO | WO 2006/109588 | 10/2006 |
| WO | 2008073186 A9 | 6/2008 |
| WO | WO 2009/110245 | 9/2009 |
| WO | WO 2009/149027 | 12/2009 |
| WO | WO 2010/013696 | 2/2010 |

OTHER PUBLICATIONS

Chinese Office Action dated Feb. 2, 2015 which issued during prosecution of CN Application No. 201280062762.3.

Office Action dated Apr. 1, 2015 which issued during prosecution of U.S. Appl. No. 14/357,145.

Office Action dated Apr. 1, 2015 which issued during prosecution of U.S. Appl. No. 14/357,172.

Chinese Office Action dated Sep. 22, 2015 during the prosecution of Chinese Patent Application No. 201280062750.0.

Chinese Office Action dated Sep. 22, 2015 during the prosecution of Chinese Patent Application No. 201280062762.3.

Japanese Office Action dated Nov. 25, 2015 during the prosecution of Japanese Patent Application No. 2012-522686.

Chinese Office Action dated Oct. 30, 2014, which issued during prosecution of Chinese Application No. 201180071600.1.

Crespo, et al., "Extraction of Hydrocarbons from Seaweed Samples Using Sonication and Microwave—Assisted Extraction: A Comparative Study", Journal of Chromatographic Science, 2006, vol. 44, No. 10, p. 615-618.

Hattab, et al., "Comparison of various extraction methods for identification and determination of volatile metabolites from the brown alga Dictyopteris membranacea", Journal of Chromatography A, 2007, vol. 1143, p. 1-7.

Hattab, et al., "Isolation of the Volatile Compounds from the Brown Alga Dictyopteris membranacea by Focused Microwave-Assisted Hydrodistillation", J. Essent. Oil Res., 2002, vol. 14, No. 6, p. 422-424.

(56) References Cited

OTHER PUBLICATIONS

International Search Report dated Jan. 29, 2013, from corresponding International Application No. PCTJP2012/079152.
Itaya et al., "Effect of Scattering by Fluidization of Electrically Conductive Beads on Electrical Field Intensity Profile in Microwave Dryers" 2005, Drying Technology, 23, p. 273-287.
Uy F. Sandra, et al., "Seaweed processing using industrial single-mode cavity microwave heating: a preliminary investigation", Carbohydrate Research, 2005, vol. 340, No. 7, p. 1357-1364.
International Search Report dated Aug. 23, 2011, which issued during the prosecution of International Application No. PCT/JP2011/064965.
Written Opinion dated Aug. 23, 2011, which issued during the prosecution of International Application No. PCT/JP2011/064965.
Japanese Office Action, dated Aug. 3, 2011, which issued during the prosecution of Japanese Patent Application No. 2010-111270.
Japanese Office Action, dated Oct. 31, 2013, which issued during the prosecution of Japanese Patent Application No. 2010-111271.
Japanese Search Report, dated May 31, 2010, prepared for Japanese Patent Application No. 2010-111270.
Japanese Search Report, dated Jun. 2, 2010, prepared for Japanese Patent Application No. 2010-111271.
Chinese Office Action dated Jun. 25, 2015, which issued during prosecution of Chinese Appl. No. 201180071600.1.
U.S. Office Action dated Jul. 9, 2015 which issued during prosecution of U.S. Appl. No. 13/807,865.
Extended European Search Report dated Jul. 13, 2015 which issued during prosecution of EP Application No. 12848355.9.
Extended European Search Report dated Jul. 20, 2015 which issued during prosecution of EP Application No. 12848048.0.
U.S. Office Action dated Aug. 18, 2015 which issued during prosecution of U.S. Appl. No. 14/357,145.
U.S. Office Action dated Aug. 19, 2015 which issued during prosecution of U.S. Appl. No. 14/357,172.
Search report issued in Brazilian Application BR112013033215-8 dated May 18, 2018. With English Translation.
Office Action issued in U.S. Appl. No. 14/123,174 dated Jul. 19, 2018.
Technical Examination Report dated Oct. 9, 2018_BR112013033215-8 & Machine translation (9 pages).
Office Action dated Aug. 28, 2018 in U.S. Appl. No. 15/398,877.
Notification of Result of Substantive Examination issued for Indonesian Patent Application No. P-00201400520 dated Jan. 18, 2019.
Final Office Action issued for U.S. Appl. No. 15/398,877 dated Feb. 11, 2019.
Communication issued for European Patent Application No. 11868832.4 dated Feb. 26, 2019.
First Examination Report for Indian Application No. 534/CHENP/2014 dated Nov. 15, 2018.
Office Action for U.S. Appl. No. 13/807,865 dated Nov. 26, 2018.
Communication pursuant to Article 94(3) EPC for European Patent Application No. 12848355.9 dated Dec. 12, 2018.
Communication pursuant to Article 94(3) EPC issued in corresponding European Patent Application No. 12848048.0 dated Jul. 22, 2019.
Office Action issued in corresponding U.S. Appl. No. 16/655,533 dated Sep. 28, 2020.
Office Action issued in corresponding U.S. Appl. No. 16/655,533 dated Mar. 11, 2021.
Hearing Notice in Reference of Application No. 534/CHENP/2014 issued in corresponding Indian Patent Application dated Dec. 10, 2019.
Summons to attend oral proceedings pursuant to Rule 115(1) EPC issued in corresponding European Patent Application No. 12 848 355.9 dated Jan. 24, 2020.
Communication pursuant to Article 94(3) EPC issued in corresponding EP Patent Application No. 12 848 048 dated Oct. 26, 2020.

\* cited by examiner

CHEMICAL REACTION APPARATUS AND CHEMICAL REACTION METHOD

CROSS-REFERENCE TO RELATED APPLICATION

This is a U.S. national phase application under 35 U.S.C. § 371 of International Patent Application No. PCT/JP2011/064965, filed on Jun. 29, 2011. The International Application was published on Jan. 3, 2013, as International Publication No. WO 2013/001629 under PCT Article 21(2). The entire content of the International Application is hereby incorporated by reference.

TECHNICAL FIELD

The present invention relates to a chemical reaction apparatus and the like for irradiating microwaves in a reactor.

BACKGROUND ART

Conventionally, chemical reaction apparatuses and chemical reaction methods, which perform heat treatment and the like by irradiating a reaction material with microwaves (e.g., electromagnetic waves), are known. See, for example, Japanese Patent Application Publication No. JP 2006-516008A.

In such conventional chemical reaction apparatuses and the like, there has been a demand for further facilitating a chemical reaction by more efficiently irradiating microwaves.

The present invention was arrived at in view of these circumstances, and it is an aspect thereof to provide a chemical reaction apparatus and the like capable of more efficiently irradiating the content inside a reactor with microwaves.

SUMMARY

In order to achieve the above-described aspect, the present invention is directed to a chemical reaction apparatus, including a horizontal flow-type reactor in which a content horizontally flows with an unfilled space being provided thereabove, a microwave generator that generates microwaves, and at least one waveguide that transmits the microwaves generated by the microwave generator to the unfilled space in the reactor.

With this configuration, microwaves can be irradiated over a larger surface area. As a result, the content can be efficiently irradiated with microwaves, and the reaction of the content can be facilitated.

Furthermore, the chemical reaction apparatus according to the present invention may further include at least one agitation unit that agitates the content inside the reactor.

With this configuration, the content is agitated, and, thus, the content inside the reactor can be more uniformly irradiated with microwaves. As a result, for example, a situation can be avoided in which only part of the content inside the reactor is irradiated with microwaves.

Furthermore, in the chemical reaction apparatus according to the present invention, the agitation unit may perform agitation using at least any one method of rotating agitation, bubbling agitation, and ultrasonic wave agitation.

Furthermore, in the chemical reaction apparatus according to the present invention, the reactor may allow a raw material and a solid catalyst to flow therein, and the chemical reaction apparatus may further include a catalyst separating portion that separates the solid catalyst from a product material after a reaction in the reactor.

With this configuration, a product material after the reaction from which the solid catalyst has been separated can be obtained.

Furthermore, the chemical reaction apparatus according to the present invention may further include a mixing portion that mixes a raw material and a solid catalyst, and the raw material and the solid catalyst mixed by the mixing portion may be loaded into the upstream side in the reactor.

With this configuration, the raw material and the solid catalyst are mixed before being loaded into the reactor, and, thus, the reaction inside the reactor is further facilitated.

Furthermore, in the chemical reaction apparatus according to the present invention, the solid catalyst may be microwave-absorbing or microwave-sensitive.

With this configuration, the solid catalyst is more efficiently heated, and, thus, the reaction of the raw material near the solid catalyst is further facilitated.

Furthermore, in the chemical reaction apparatus according to the present invention, the reactor may have multiple chambers that are continuously arranged in series.

With this configuration, the content undergoes a reaction while being retained in each chamber. As a result, the content can be effectively irradiated with microwaves in each chamber, and, thus, a situation can be avoided in which unreacted raw material is discharged from the reactor (i.e., a situation in which the raw material flows as it is from the inlet to the outlet of the reactor).

Furthermore, in the chemical reaction apparatus according to the present invention, the reactor may have multiple partition plates that partition the inside of the reactor into multiple chambers, and the partition plates may be provided with a flow path through which the content flows from the upstream side to the downstream side.

With this configuration, multiple chambers in the reactor can be realized by the partition plates.

Furthermore, in the chemical reaction apparatus according to the present invention, the flow path may be a flow path that allows the content to flow over each of the partition plates or a flow path that allows the content to flow through a void of each of the partition plates.

Furthermore, in the chemical reaction apparatus according to the present invention, the partition plates may each transmit microwaves.

With this configuration, microwaves are irradiated even through the partition plates, and, thus, the content can be more efficiently irradiated with microwaves.

Furthermore, in the chemical reaction apparatus according to the present invention, the waveguide may be provided at a location of the partition plates.

With this configuration, microwaves can be irradiated through one waveguide on two chambers that have been partitioned by the partition plates. As a result, microwaves can be more efficiently irradiated.

Furthermore, the chemical reaction apparatus according to the present invention may further include multiple temperature measuring portions that measure a temperature inside each chamber in the reactor, and a microwave control portion that controls a power of microwaves with which each chamber is to be irradiated, according to the temperature measured by each of the temperature measuring portions.

With this configuration, the temperature of each chamber can be kept at a desired temperature.

Furthermore, in the chemical reaction apparatus according to the present invention, the number of the microwave generator provided may be at least two, and the at least two microwave generators may generate microwaves having at least two frequencies.

With this configuration, microwaves can act on a wider range of materials.

The chemical reaction apparatus and the like according to the present invention can more efficiently irradiate a content with microwaves, and can facilitate the reaction of the content.

DETAILED DESCRIPTION

Figure 1:
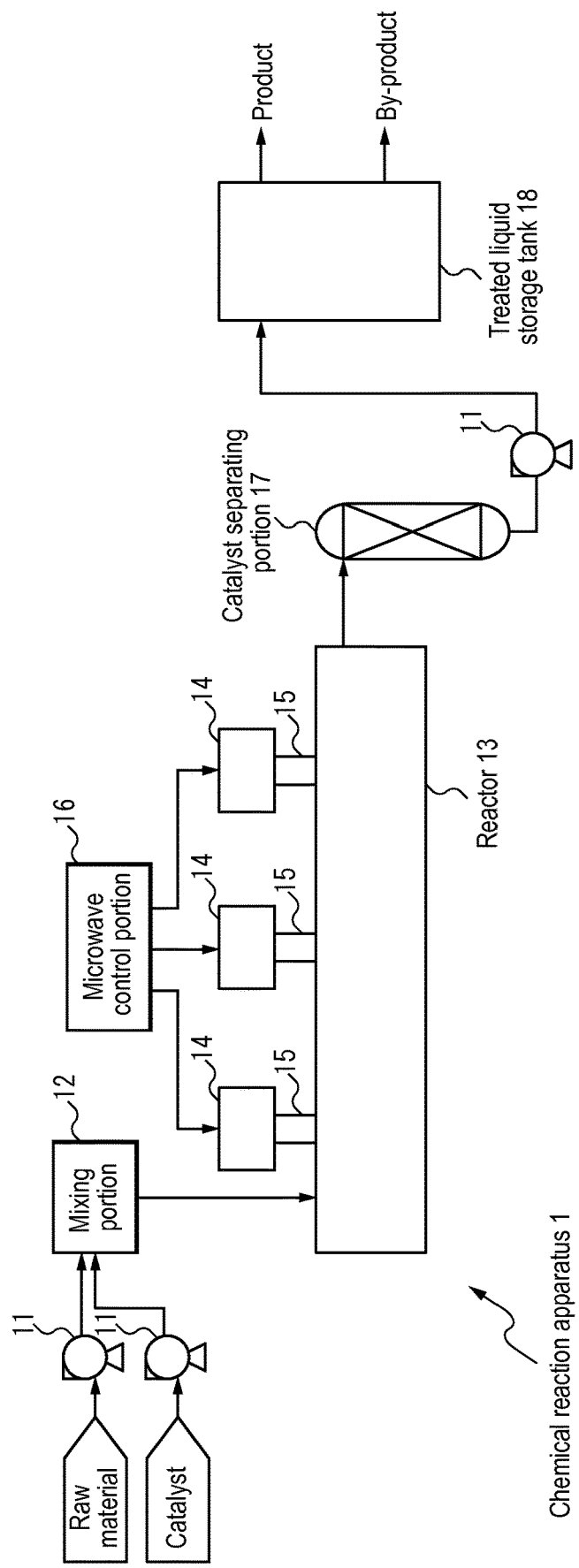
FIG. 1 is a diagram showing the configuration of a chemical reaction apparatus according to an example of the present invention.

Hereinafter, a chemical reaction apparatus according to the present invention will be described by way of an example. Note that constituent elements denoted by the same reference numerals are the same as or similar to each other in the following example, and, thus, a description thereof may not be repeated.

EXAMPLE

Below, a chemical reaction apparatus according to an example of the present invention will be described with reference to the drawings. The chemical reaction apparatus according to this example irradiates the content of a reactor with microwaves.

FIG. 1 is a diagram showing the configuration of a chemical reaction apparatus 1 according to this example. The chemical reaction apparatus 1 according to this example includes a mixing portion 12, a reactor 13, microwave generators 14, waveguides 15, a microwave control portion 16, a catalyst separating portion 17, and a treated liquid storage tank 18.

The mixing portion 12 mixes a raw material and a solid catalyst. The mixing portion 12 may mix the raw material and the like with a reactant. The raw material may contain multiple materials. For example, in the case of performing esterification in the reactor 13, fat and oils and alcohol may be used as the raw material. The raw material and the solid catalyst may be supplied to the mixing portion 12 by pumps 11 as shown in FIG. 1, or may be supplied to the mixing portion 12 using other methods. The mixing portion 12 may mix two or more materials, for example, by rotating a blade-like member, a wing-like member, or a screw-like member. Note that, although this example describes the case in which the catalyst that is to be mixed with the raw material is a solid catalyst (heterogeneous catalyst), the catalyst may be a liquid catalyst (homogeneous catalyst). Furthermore, the solid catalyst may or may not form a fluidized bed inside the reactor 13. Furthermore, there is no limitation on the shape of the solid catalyst. Examples of the shape of the solid catalyst include various grains, a cylinder (that may or may not be hollow), a sphere, a pellet, a ring, a shell, and other shapes. Furthermore, the solid catalyst may or may not be, for example, microwave-absorbing or microwave-sensitive. If the solid catalyst is microwave-absorbing or microwave-sensitive, when microwaves are irradiated inside the reactor 13 (described later), the solid catalyst is heated by the microwaves, and the chemical reaction near the solid catalyst is facilitated. Note that the microwave absorptivity and the microwave sensitivity depend on the frequency of microwaves used for irradiation, the temperature inside the reactor 13, and the like. That is to say, materials that have a high dielectric loss factor, at the frequency of microwaves used and the temperature inside the reactor 13 in which the raw material is to undergo a reaction, provide a high microwave absorptivity. Accordingly, for example, a solid catalyst containing such a highly microwave-absorbing material may be used. For example, if microwaves at 2.45 GHz are irradiated, examples of the microwave-absorbing material include carbon except for fullerene (e.g., graphite, carbon nanotube, activated carbon, etc.), iron, nickel, cobalt, ferrite, and the like. Accordingly, the solid catalyst may contain such a microwave-absorbing material. Specifically, the solid catalyst may be a composite in which such a microwave-absorbing or microwave-sensitive material and a metal or metal oxide are combined, a composite in which such a microwave-absorbing or microwave-sensitive material and a catalyst such as alkali catalyst or acid catalyst are combined, or a composite in which a microwave-absorbing or microwave-sensitive material, a catalyst such as alkali catalyst or acid catalyst, and a metal or metal oxide are combined. The composite may be formed, for example, through physical adsorption, chemical bonding, alloying, or other methods. Furthermore, in the mixing portion 12, preliminary heating may or may not be performed for preparation for the reaction in the reactor 13. In the case of performing the preliminary heating, the temperature in the preliminary heating in the mixing portion 12 is preferably controlled so as to be at a desired temperature or in a desired temperature range at the time when the raw material and the like enter the reactor 13. Note that, in the case of not performing the preliminary heating in the mixing portion 12, heating corresponding to the preliminary heating may be performed in the reactor 13. The raw material and the solid catalyst mixed by the mixing portion 12 are loaded into the upstream side in the reactor 13.

The reactor 13 is a horizontal flow-type reaction unit in which the content horizontally flows with an unfilled space being provided thereabove. Examples of the content include a mixture of the raw material and the catalyst. The raw material and the catalyst mixed by the mixing portion 12 flow inside the reactor 13. Note that, since the chemical reaction in the reactor 13 produces a product material from the raw material, the content of the reactor 13 may be considered to contain the product material. That is to say, the content may be referred to as the raw material and/or the product material. Furthermore, since an unfilled space is present above the content, the content is typically a material other than gas, that is, solid or liquid. Typically, the content is liquid. The inner wall of the reactor 13 is preferably made of a material that reflects microwaves. Examples of the material that reflects microwaves include metal. The internal configuration of the reactor 13 will be described later.

The microwave generators 14 generate microwaves. The chemical reaction apparatus 1 according to this example may include one microwave generator 14, or may include two or more microwave generators 14. There is no limitation on the frequency of the microwaves, and examples thereof include 2.45 GHz, 5.8 GHz, 24 GHz, 913 MHz, and other frequencies ranging from 300 MHz to 300 GHz.

The waveguides 15 transmit the microwaves generated by the microwave generators 14 to the unfilled space in the reactor 13. Typically, the number of waveguides 15 provided is the same as the number of microwave generators 14 as shown in FIG. 1. Note that the standard of the waveguides 15 is preferably in accordance with the frequency of the microwaves generated by the microwave generators 14.

The microwave control portion 16 controls the power of microwaves with which the reactor 13 is to be irradiated, according to the temperature measured by temperature measuring portions 25 (described later). The control by the microwave control portion 16 makes it possible to keep inside the reactor 13 at a desired temperature or in a desired temperature range.

The catalyst separating portion 17 separates the catalyst from the product material after the reaction in the reactor 13. If the catalyst that has been mixed with the raw material is a solid catalyst, for example, filtering may be used to separate the solid catalyst, or one of the solid catalyst and the product material may be precipitated to separate the solid catalyst. Furthermore, if the solid catalyst contains a magnetic substance, a magnet (that may be a permanent magnet or may be an electromagnet) for attracting the solid catalyst may be used to separate the solid catalyst. Note that the separated solid catalyst may be used again as appropriate. Furthermore, if a liquid catalyst is used, distillation, extraction, or neutralization may be performed in the catalyst separating portion 17 to separate the catalyst.

The product material from which the catalyst has been separated by the catalyst separating portion 17 is loaded into the treated liquid storage tank 18. Then, this product material is separated as appropriate into a final product, a by-product, and the like. For example, if the raw material is free fatty acid, and esterification is performed in the reactor 13, a product that is biodiesel fuel and a by-product that is water are obtained. In this case, an acid catalyst is used. Furthermore, for example, if the raw material is triglyceride, and transesterification is performed in the reactor 13, a product that is biodiesel fuel and a by-product that is glycerin are obtained. In this case, an alkali catalyst is used.

Note that a cooler (not shown) that cools down the material after the reaction in the reactor 13 may or may not be provided on the path after the reactor 13. In the former case, for example, the cooler may use water to cool down the material after the reaction in the reactor 13.

Figure 2:
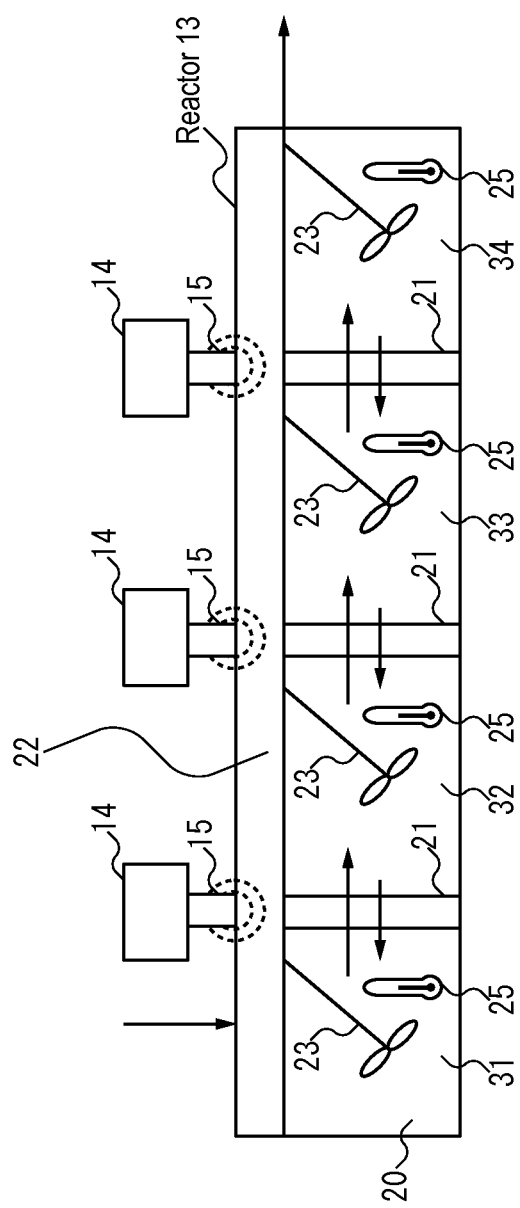
FIG. 2 is a diagram showing an exemplary internal configuration of a reactor according to the example.

FIG. 2 is a diagram showing an exemplary internal structure of the reactor 13 according to this example. In FIG. 2, the reactor 13 has multiple chambers 31, 32, 33, and 34 that are continuously arranged in series. The chambers 31 to 34 have been partitioned from each other by multiple partition plates 21 that partition the inside of the reactor 13. As described above, an unfilled space 22 is present in the upper portion inside the reactor 13. The unfilled space 22 is irradiated with the microwaves generated by the microwave generators 14 and transmitted via the waveguides 15. The waveguides 15 may be arranged respectively at the positions of the partition plates 21 as shown in FIG. 2, or may be arranged in different manner. In the former case, for example, the microwaves that have been transmitted by one waveguide 15 to the unfilled space 22 are mainly irradiated on two chambers that have been partitioned from each other by the partition plate 21 at the position corresponding to that waveguide 15. The partition plates 21 may transmit microwaves, may absorb microwaves, or may reflect microwaves. Examples of the material that transmits microwaves include Teflon (registered trademark), quartz glass, ceramic, silicon nitride-alumina, and the like. Accordingly, the partition plates 21 that transmit microwaves may be made of such a material that transmits microwaves. Furthermore, examples of the material that absorbs microwaves include carbon except for fullerene, and the like. Accordingly, the partition plates 21 that absorb microwaves may be made of such a material that absorbs microwaves. Furthermore, examples of the material that reflects microwaves include metal. Accordingly, the partition plates 21 that do not transmit microwaves may be made of such a material that reflects microwaves. Furthermore, the partition plates 21 may be made of a combination of two or more materials freely selected from the material that transmits microwaves, the material that absorbs microwaves, and the material that reflects microwaves.

Figure 3A:
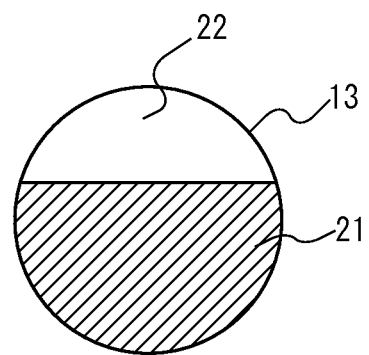
FIG. 3A is a view showing an exemplary partition plate according to the example.
Figure 3B:
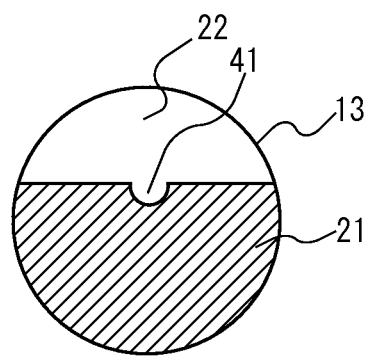
FIG. 3B is a view showing an exemplary partition plate according to the example.
Figure 3C:
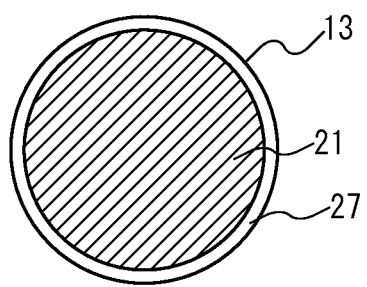
FIG. 3C is a view showing an exemplary partition plate according to the example.
Figure 3D:
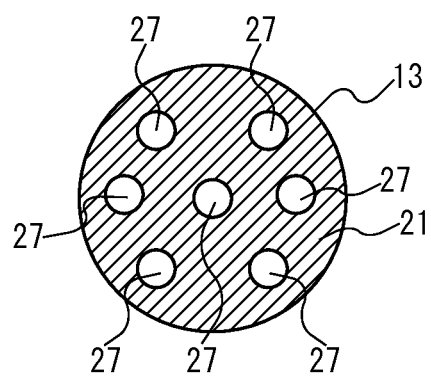
FIG. 3D is a view showing an exemplary partition plate according to the example.
Figure 3E:
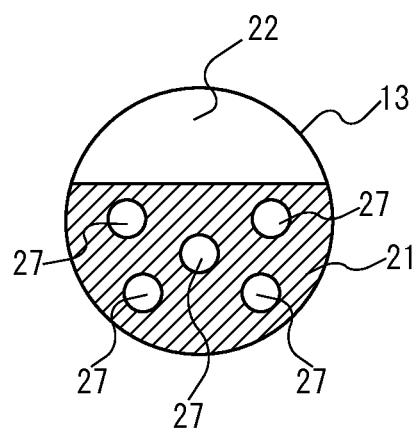
FIG. 3E is a view showing an exemplary partition plate according to the example.
Figure 3F:
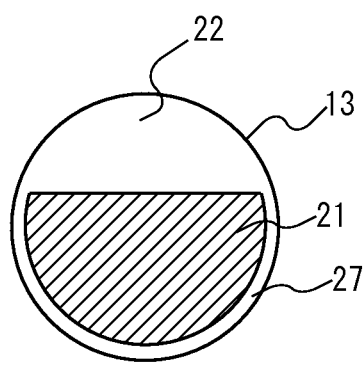
FIG. 3F is a view showing an exemplary partition plate according to the example.

A content 20 such as the raw material and the like loaded into the reactor 13 flows through the chambers 31 to 34 and is finally discharged from the downstream side (the right end of the reactor 13 in FIG. 2). Note that a flow path that allows the content to flow is formed at the partition plates 21. The flow path allows the content to flow mainly from the upstream side (the left side in FIG. 2) to the downstream side (the right side in FIG. 2) in the reactor 13, but may allow part of the content to flow from the downstream side to the upstream side as indicated by the lower arrows in FIG. 2. The flow path at the partition plates 21 may allow the content, for example, to flow over each of the partition plates 21, or to flow through a void in or around each of the partition plates 21. FIG. 3A to FIG. 3F are views showing the partition plate 21 provided in the reactor 13 in the shape of a cylinder, in the length direction of the reactor 13. In the case of an overflow-type flow path, for example, the partition plate 21 may not be present at the position of the unfilled space 22 as shown in FIGS. 3A and 3B, and the content may flow through that position (i.e., over the partition plates 21). In that case, as shown in FIG. 3B, the upper side of the partition plate 21 may be provided with a recess portion 41 through which the content flows. With that configuration, for example, even in the case where the liquid surface of the content 20 is at the same level as the upper side of the partition plate 21, the content flows through the cutout of (portion that has been cut out from) the recess portion 41. Note that there is no limitation on the shape of the recess portion 41. FIG. 3B shows the case in which the recess portion 41 is in the shape of a semicircle, and examples of the shape of the cutout of the recess portion 41 include a triangle, a rectangle, and other shapes. Furthermore, there is no limitation on the number of recess portions 41. For example, the number may be one as in FIG. 3B, or may be two or more. Furthermore, in the case of a void-type flow path, for example, a void 27 may be present between the partition plate 21 and the inner wall of the reactor 13 as shown in FIG. 3C, or voids 27 may be present in the partition plate 21 itself as shown in FIG. 3D. Each void 27 preferably has a size that at least allows the content to flow through the void. Note that there is no limitation on the shape and the number of voids 27. FIG. 3C shows the case in which the void 27 is in the shape of a ring, and examples of the shape of the void 27 include a C shape with part of the ring being blocked. Furthermore, FIG. 3D shows the case in which each of the voids 27 is in the shape of a circle, and examples of the shape of the voids 27 include a triangle, a rectangle, and other shapes. Furthermore, the number of voids 27 may be, for example, larger than or smaller than that shown in FIG. 3D (i.e., may be one or may be two or more). Furthermore, as shown in FIGS. 3E and 3F, the flow path of the overflow-type and the flow path through the void 27 of the partition plate 21 may be combined. Note that the reactor 13 may or may not be inclined so as to be lower from the upstream side toward the downstream side.

Furthermore, as shown in FIG. 2, the reactor 13 has agitation units 23. That is to say, the chemical reaction apparatus 1 according to this example has one or more agitation units 23 that agitate the content inside the reactor 13. FIG. 2 shows the case in which the chambers 31 to 34 respectively have the agitation units 23, but there is no limitation to this. One or more chambers may not have the agitation unit 23. Furthermore, FIG. 2 shows the case in which each of the agitation units 23 is in the shape of a blade, but this merely schematically shows the agitation units 23. Examples of the agitation units 23 include a rotating agitation unit, a bubbling agitation unit, an ultrasonic wave agitation unit, and combinations of any two or more thereof. If the agitation units 23 perform rotating agitation, the agitation may be performed, for example, by rotating a blade-like member, a wing-like member, a rod-like member, or the like. The blade-like member, the wing-like member, the rod-like member, or the like may transmit microwaves, may absorb microwaves, or may reflect microwaves, or may be made of a combination of two or more materials freely selected from the material that transmits microwaves, the material that absorbs microwaves, and the material that reflects microwaves. The rotation may be performed, for example, by rotating a blade-like member or the like attached to a shaft in accordance with the rotation of the shaft, or by using a magnetic force as in the case of a magnetic stirrer. In the former case using a shaft, the shaft may be provided independently for each chamber, or may be shared by multiple chambers. In the latter case using a magnetic force, a magnetic stirrer in the shape of a rod, a blade, a wing, or the like is rotated by a magnet. Furthermore, if the rotating agitation is performed using a blade-like member or a wing-like member, these members may or may not be rotated to cause the content of the reactor 13 to flow in a direction from the upstream to the downstream or in its opposite direction. Furthermore, if the agitation units 23 perform bubbling agitation, the agitation may be performed, for example, by blowing gas into the content inside the reactor 13. Examples of the gas that is to be blown into the content include inert gases such as helium or argon, nitrogen, air, and the like. Furthermore, if the agitation units 23 perform ultrasonic wave agitation, the agitation may be performed, for example, by generating ultrasonic waves on a bottom face or a side face of the reactor 13 and then irradiating the content of the reactor 13 with the generated ultrasonic waves. Note that rotating agitation, bubbling agitation, and ultrasonic wave agitation are already known, and, thus, a detailed description thereof has been omitted. Furthermore, the agitation units 23 may perform the agitation using an agitation method other than the above. For example, the agitation units 23 may perform swinging agitation that swings the reactor 13 itself.

Hereinafter, reasons why the content of the reactor 13 is agitated by the agitation units 23 will be briefly described. A first reason why the content is agitated by the agitation units 23 is to uniformly heat the content with microwaves. Although depending on the type of content and the temperature of the content, the depth to which microwaves penetrate is fixed, and, thus, the agitation is performed in order to uniformly irradiate and uniformly heat the entire content with microwaves. Furthermore, the content can be more efficiently irradiated with microwaves as the surface area of the content at the unfilled space 22 increases. Accordingly, a second reason why the content is agitated is to increase the area subjected to microwave irradiation. Thus, the content is agitated by the agitation units 23 preferably at an intensity that allows the surface of the content at the unfilled space 22 to be disordered, but there is no limitation to this (if the agitation is performed for the first reason, it may be sufficient that the entire content is eventually heated). Furthermore, since the raw material and the like are agitated using the agitation units 23 in this manner, even in the case where a raw material contains two or more materials having different densities, these materials can be mixed and reacted with each other as appropriate. For example, when causing materials having different densities, such as alcohol and waste oil, to react with each other in a vertical flow-type reactor, these materials are easily separated from each other. However, as in this example, if the reactor 13 is of a horizontal flow-type and is provided with the agitation units 23, these materials can be mixed and reacted with each other as appropriate. Furthermore, if the reactor 13 is provided with multiple agitation units 23, the types of agitation performed by these agitation units may be the same or may be different from each other. In the latter case, for example, rotating agitation may be performed in the chamber 31, bubbling agitation may be performed in the chamber 32, and ultrasonic wave agitation may be performed in the chamber 33.

Furthermore, as shown in FIG. 2, the reactor 13 also has the temperature measuring portions 25. That is to say, the chemical reaction apparatus 1 according to this example may have the temperature measuring portions 25 that measure the temperature inside the reactor 13. The temperature inside the reactor 13 is preferably the temperature of the content of the reactor 13. FIG. 2 schematically shows the case in which the chambers 31 to 34 respectively have the temperature measuring portions 25, but there is no limitation to this. One or more chambers may not have the temperature measuring portion 25. Furthermore, FIG. 2 merely schematically shows the temperature measuring portions 25. The temperature measuring portions 25 may measure the temperature, for example, using a thermocouple, an infrared sensor, an optical fiber, or other methods. The temperature measured by the temperature measuring portions 25 (strictly speaking, data indicating the temperature) is passed to the microwave control portion 16, and is used to control the power of microwaves from the microwave generators 14. As described above, this control may be control for keeping the temperature of the chambers 31 to 34 at a desired temperature or in a desired temperature range. For example, if microwaves are irradiated on the position of each partition plate 21 as shown in FIG. 2, the power of microwaves irradiated on that position may be controlled, for example, using one or both of the temperatures of two chambers that have been partitioned from each other by the partition plate 21 at the position subjected to the microwave irradiation. In the former case, for example, the control may be performed using a lower temperature, using a higher temperature, or using a temperature of a chamber specified in advance. In the latter case, for example, the control may be performed using an average of these temperatures.

In the reactor 13 of this example, the height of the liquid surface of the content 20 may be, for example, 1/10 to 9/10 of the maximum height inside the reactor 13. That is to say, the height of the unfilled space 22 may be, for example, 1/10 to 9/10 of the maximum height inside the reactor 13. Furthermore, the height of the liquid surface of the content 20 may be, for example, 1/5 to 4/5 of the maximum height inside the reactor 13. Note that, if the void 27 is present as in the partition plates 21 in FIGS. 3C to 3F, the height of the liquid surface is determined by the position of the outlet via which the product material and the like are discharged from the reactor 13. Accordingly, it is sufficient that the position of the outlet is set at a position corresponding to a desired height of the liquid surface. That is to say, it is sufficient that the position of the outlet of the reactor 13 is set such that a desired unfilled space 22 can be ensured. Meanwhile, if the raw material and the like flow over the partition plates 21 as in FIGS. 3A and 3B, the height of the liquid surface in the chambers 31 to 33 other than the chamber 34 on the most downstream side is determined by the height of the partition plates 21 (also in this case, the height of the liquid surface in the chamber 34 on the most downstream side is determined by the position of the outlet). Accordingly, it is sufficient that the partition plates 21 having a height corresponding to a desired height of the liquid surface are provided inside the reactor 13. That is to say, it is sufficient that the height (position) of the overflow-type flow path over the partition plates 21 is set such that a desired unfilled space 22 can be ensured. It will be appreciated that, as long as the content 20 is irradiated with microwaves as appropriate, the height of the liquid surface of the content 20 and the height of the unfilled space 22 are not limited to those described above.

Furthermore, there is no limitation on the shape of the reactor 13. Examples of the shape of the reactor 13 include a cylinder that is elongated in the left-right direction in FIG. 2, a rectangular solid, and other shapes. In this example, a case will be described in which the reactor 13 is in the shape of a cylinder. Also in FIG. 3A to FIG. 3F, as described above, the partition plates 21 in the case in which the reactor 13 is in the shape of a cylinder have been described.

Furthermore, the wall face of the reactor 13 may be covered by a heat insulating material. In that case, heat inside the reactor 13 can be prevented from being dissipated to the outside.

Next, an operation of the chemical reaction apparatus 1 according to this example will be briefly described. The raw material and the catalyst are supplied by the pumps 11 to the mixing portion 12, are mixed in the mixing portion 12, and are loaded into the reactor 13. The speed of the raw material and the like supplied to the reactor 13 may be determined in advance.

The raw material and the like supplied to the reactor 13 flow from the upstream side to the downstream side while being agitated by the agitation units 23. At that time, the microwaves generated by the microwave generators 14 are transmitted via the waveguides 15 to the unfilled space 22 in the reactor 13, and are irradiated on the raw material and the like. As a result, the raw material and the like are heated, and the reaction of the raw material and the like is facilitated. Note that the temperatures of the chambers 31 to 34 are measured by the temperature measuring portions 25, and are passed to the microwave control portion 16 via a route that is not shown. Then, the microwave control portion 16 controls the power of the microwave generators 14 such that the temperatures of the chambers 31 to 34 are at a desired temperature or in a desired temperature range.

The product material discharged from the reactor 13 is loaded into the catalyst separating portion 17 where the catalyst is separated therefrom. Then, the product material from which the catalyst has been separated is loaded by the pump 11 into the treated liquid storage tank 18. In the treated liquid storage tank 18, the product material is separated into a target product and a by-product. In this manner, a final product is obtained. Furthermore, such treatment is repeatedly performed, and, thus, a target product is sequentially produced.

Note that the treatment that separates the catalyst in the catalyst separating portion 17 and the treatment that separates the product material into a product and a by-product in the treated liquid storage tank 18 may be performed sequentially each time the product material is loaded, or may be performed at a time when the amount of product material loaded accumulates and reaches a certain amount. That is to say, the treatment in the reactor 13 is of a flow-type (flow through-type), but the treatment in the catalyst separating portion 17 and the treated liquid storage tank 18 on the path thereafter may be of a flow-type, or may be of a batch type.

Furthermore, there is no limitation on the chemical reaction caused to occur in the chemical reaction apparatus 1 according to this example, as long as it is a chemical reaction that is caused to occur by microwave irradiation itself or by heat due to microwave irradiation. For example, the chemical reaction may be production of biodiesel fuel through esterification or transesterification, may be production of ink raw material that is ester, or may be other chemical reactions.

Next, the treatment that produces biodiesel fuel (fatty acid methyl ester) from waste oil using the chemical reaction apparatus 1 according to this example will be described by way of examples. It will be appreciated that the present invention is not limited to these examples.

Reaction System Construction Example

In this example, as the raw material, a mixture of fat and oils and free fatty acid, and alcohol were used. The alcohol was used as a reactant. The raw material and the catalyst were sent by the pumps 11 into the mixing portion 12, and were uniformly mixed. The mixed liquid was supplied to the reactor 13. The mixed liquid inside the reactor 13 was irradiated with the microwaves generated by the microwave generators 14, and, thus, the esterification reaction was facilitated. Furthermore, the mixed liquid inside the reactor 13 was loaded into the chambers 31 to 34 that had been partitioned from each other by the partition plates 21 inside the reactor 13. The mixed liquid together with the catalyst was irradiated with microwaves while being agitated by the agitation units 23, and, thus, the reaction progresses. The microwaves were irradiated on the unfilled space 22 inside the reactor 13, and were diffused inside the reactor 13. The reaction liquid in each chamber moved to its next chamber through a flow path provided at the partition plates 21. The reaction liquid was held inside the reactor 13 for a certain retention time, and then was discharged out of the reactor 13. The mixed liquid after the reaction discharged out of the reactor 13 was supplied to the catalyst separating portion 17.

After the catalyst was separated in the catalyst separating portion 17, the mixed liquid was loaded into the treated liquid storage tank 18. From the reaction liquid after the catalyst separation, water and glycerin that were by-products were further separated in the treated liquid storage tank 18, and, thus, crude methyl ester that was a target product was obtained.

Esterification Reaction of Industrial Waste Oil

Hereinafter, a typical example of an esterification reaction of free fatty acid using industrial waste oil will be described. Industrial waste oil containing 34 wt % of free fatty acid (also containing triglyceride, pitch fraction, and the like), 2.8 molar equivalents of methanol (the molar equivalents obtained by calculating the free fatty acid in the industrial waste oil as oleic acid) as a reactant, and 3 wt % of solid acid catalyst (the percentage by weight with respect to the industrial waste oil) were mixed in the mixing portion 12. Then, the mixture was supplied to the reactor 13. The supply speed to the reactor 13 was set at about 1.2/h in the space velocity described below. Note that "capacity of reaction unit" in this example refers to a capacity obtained by subtracting the capacity of the unfilled space 22 from the full capacity of the reactor 13.

(Space velocity)=(Volume flow rate of waste oil)/(Capacity of reaction unit)

Figure 4:
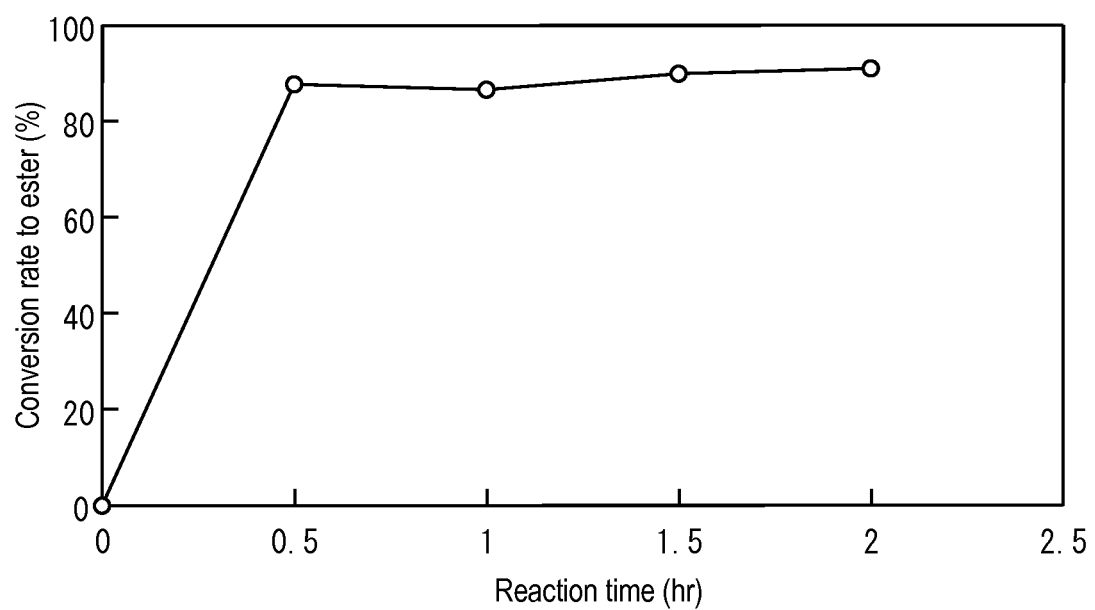
FIG. 4 is a graph showing a conversion rate to ester in an example according to the example.

The microwave power of the reactor 13 was subjected to feedback control based on the temperatures inside the chambers 31 to 34, and, thus, the temperatures of the chambers 31 to 34 were kept constant. In this experiment, the reaction temperature was set at 70° C. FIG. 4 shows a conversion rate to fatty acid methyl ester through the esterification reaction of fatty acid and methanol in this example. The equation for calculating the conversion rate to methyl ester is as follows.

Conversion rate to methyl ester (%)=[Methyl ester concentration]/[Fatty acid initial concentration]×100

As can be clearly seen from FIG. 4, the esterification reaction rapidly progressed after the start of the reaction, and the conversion rate reached 87% in 30 minutes, after which the conversion rate gradually increased, and the reaction reached substantially equilibrium in 1.5 hours. Note that no particular change was seen in the other components in the waste oil. This result shows that the esterification reaction using the flow through-type reaction unit according to this example can cause the esterification reaction to efficiently progress with respect to free fatty acid in waste oil, and can cause the reaction to stably occur in a continuous manner.

As described above, with the chemical reaction apparatus 1 according to this example, the content in the reactor 13 can be efficiently irradiated with microwaves. As a result, the chemical reaction in the reactor 13 can be facilitated. In particular, since the content inside the reactor 13 is agitated using the agitation units 23, the content can be uniformly irradiated with microwaves even in the case where the depth to which microwaves penetrate is not so deep. Furthermore, since the reactor 13 is partitioned into multiple chambers, the content undergoes a reaction while being retained in each chamber, and, thus, the content can be effectively irradiated with microwaves in each chamber. As a result, a situation can be avoided in which unreacted raw material is discharged from the reactor 13 (i.e., a situation in which the raw material flows as it is from the inlet to the outlet of the reactor 13). Furthermore, if the solid catalyst is microwave-absorbing or microwave-sensitive, the solid catalyst is efficiently heated through microwave irradiation, and, thus, the chemical reaction near the solid catalyst can be facilitated.

In this manner, the chemical reaction inside the reactor 13 is facilitated, and, thus, a product material can be more efficiently obtained.

In this example, the case has been described in which the mixing portion 12 that mixes the raw material and the catalyst is present, but there is no limitation to this. For example, if a premixture of the raw material and the catalyst is used, if the mixing is also performed by the reactor 13, if the solid catalyst that flows inside the reactor 13 is retained inside the reactor 13, or if a solid catalyst forming a fixed bed is used instead of the solid catalyst that flows inside the reactor 13, the chemical reaction apparatus 1 does not have to be provided with the mixing portion 12. Note that, if a solid catalyst forming a fixed bed is used, typically, the solid catalyst forming a fixed bed is provided inside the reactor 13. The solid catalyst forming a fixed bed may be fixed, for example, by being pasted on the inner wall of the reactor 13, or by being placed in a catalyst filled layer, a column, or the like inside the reactor 13. Examples of the shape of the solid catalyst include various grains, a cylinder (that may or may not be hollow), a sphere, a pellet, a ring, a shell, a honeycomb, a foam, a fiber, a cloth, a plate, and other shapes.

Figure 5:
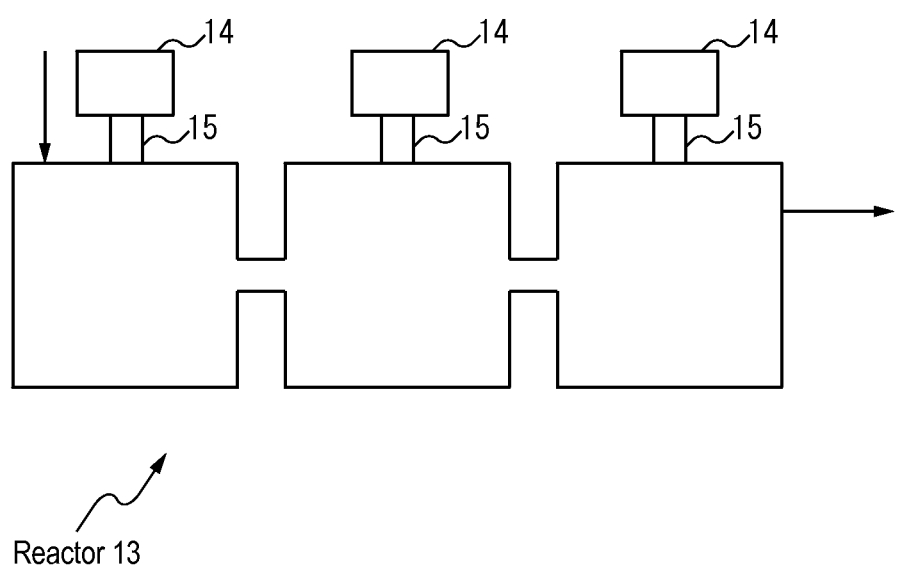
FIG. 5 is a view showing another exemplary reactor according to the example.

Furthermore, in this example, the case has been described in which the inside of the reactor 13 is partitioned by the partition plates into the multiple chambers 31 to 34, but there is no limitation to this. The reactor 13 may be configured by multiple independent chambers that are connected to each other as shown in FIG. 5. In the case of the configuration as shown in FIG. 5, microwave irradiation is preferably performed in each of the chambers. Note that the chambers may respectively have the agitation units 23 and the temperature measuring portions 25, as described above.

Furthermore, in this example, the case has been described in which the reactor 13 has four chambers 31 to 34 that are continuously arranged in series as shown in FIG. 2, or has three chambers that are continuously arranged in series as shown in FIG. 5, but there is no limitation on the number of chambers. Typically, as the number of chambers increases, a situation can be more effectively prevented in which the raw material flows as it is from the inlet to the outlet of the reactor 13. Furthermore, if the capacity of each chamber does not change regardless of an increase or a decrease in the number of chambers, the retention time from when the content of the reactor 13 flows into the reactor 13 to when the content of the reactor 13 flows out of the reactor 13 becomes longer as the number of chambers increases, and the retention time becomes shorter as the number of chambers decreases. Accordingly, in this case, the number of chambers can be adjusted such that a desired retention time is obtained.

Furthermore, in this example, the case has been described in which the reactor 13 has multiple chambers, that is, the reactor 13 is partitioned by the partition plates 21 into the multiple chambers 31 to 34, but there is no limitation to this. The reactor 13 may have only one chamber instead of multiple chambers.

Figure 6:
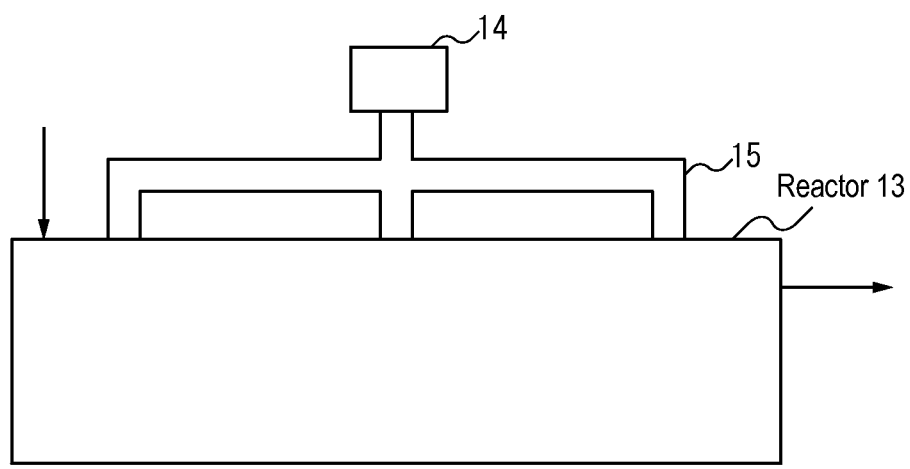
FIG. 6 is a view showing another exemplary microwave generating portion and waveguide according to the example.

Furthermore, in this example, the case has been described in which the multiple microwave generators 14 are provided, but there is no limitation to this. For example, the microwaves generated by the microwave generator 14 may be transmitted via a branched waveguide 15 to multiple locations as shown in FIG. 6. The multiple locations may be, for example, multiple chambers. FIG. 6 shows the case in which the chemical reaction apparatus 1 is provided with only one microwave generator 14, but, in the case where the chemical reaction apparatus 1 is provided with two or more microwave generators 14, the microwaves generated by any one of the multiple microwave generators 14 may be transmitted via the branched waveguide 15 to multiple locations. The same can be applied to the case in which the chambers are independent of each other as shown in FIG. 5. For example, if the microwaves generated by the microwave generators 14 are transmitted to multiple chambers, the microwave control portion 16 may control the power of the microwave generators 14 using any or all of the temperatures of the chambers to which the microwaves generated by the microwave generators 14 are transmitted. For example, the microwave control portion 16 may perform the control using an average of all temperatures of the chambers, or may perform the control using a maximum value or a minimum value of the temperatures of the chambers.

Furthermore, in this example, the case has been described in which the chemical reaction apparatus 1 is provided with the temperature measuring portions 25 and the microwave control portion 16, but there is no limitation to this. For example, if it is possible to keep the temperature inside the reactor 13 at a desired temperature or in a desired temperature range by setting the power of microwaves to a predetermined value, the control of the power of microwaves using the temperature does not have to be performed.

Furthermore, in this example, the case has been described in which the catalyst separating portion 17 is provided on the path after the reactor 13, but there is no limitation to this. If the catalyst does not have to be separated by the chemical reaction apparatus 1 according to this example, as in the case in which the catalyst is separated by another apparatus, the case in which the solid catalyst that flows inside the reactor 13 is retained inside the reactor 13, the case in which a solid catalyst forming a fixed bed is used instead of the solid catalyst that flows inside the reactor 13, or the case in which no catalyst is used in the chemical reaction in the reactor 13, the catalyst separating portion 17 does not have to be provided.

Furthermore, in this example, the case has been described in which the raw material and the catalyst are mixed and loaded into the reactor 13, but there is no limitation to this. For example, only the raw material may be loaded into the reactor 13. Furthermore, if the raw material and the catalyst are not mixed, only the raw material may flow inside the reactor 13. That is to say, the content of the reactor 13 may be, for example, a mixture of multiple raw materials. Furthermore, even in the case where the raw material and the catalyst are not mixed, for example, the raw material and the catalyst may flow inside the reactor 13 when the solid catalyst that flows inside the reactor 13 is retained inside the reactor 13. Furthermore, if the raw material and the catalyst are not mixed, the mixing portion 12 may, for example, mix the raw material, or mix the raw material (substrate) and the reactant. Furthermore, if the raw material and the like do not have to be mixed, the chemical reaction apparatus 1 does not have to be provided with the mixing portion 12 as described above.

Furthermore, in this example, the case has been described in which one or more agitation units 23 that agitate the raw material inside the reactor 13 are provided, but there is no limitation to this. For example, if the reactor 13 is configured such that the entire raw material can be easily irradiated with microwaves (e.g., if the inner diameter of the reactor 13 is small, etc.), the agitation units 23 do not have to be provided.

Furthermore, in this example, the case has been described in which the chemical reaction apparatus 1 is provided with the treated liquid storage tank 18, but there is no limitation to this. For example, a mixture of the product material and the by-product discharged from the chemical reaction apparatus 1 may be subjected to extraction of the product material and the like in another apparatus.

Figure 7A:
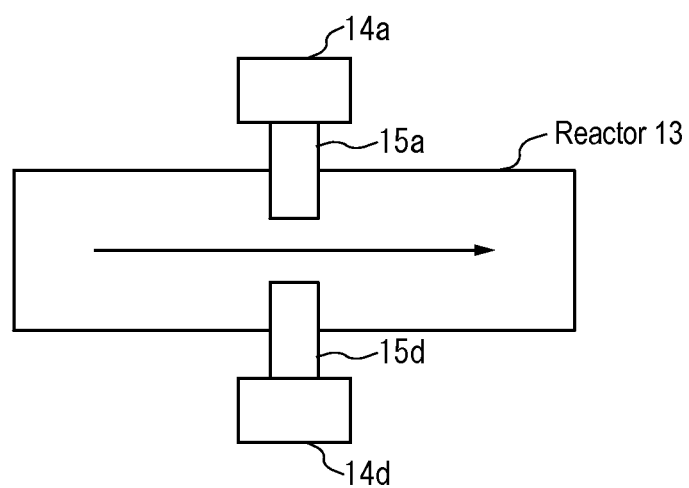
FIG. 7A is a view illustrating a position for microwave irradiation according to the example.
Figure 7B:
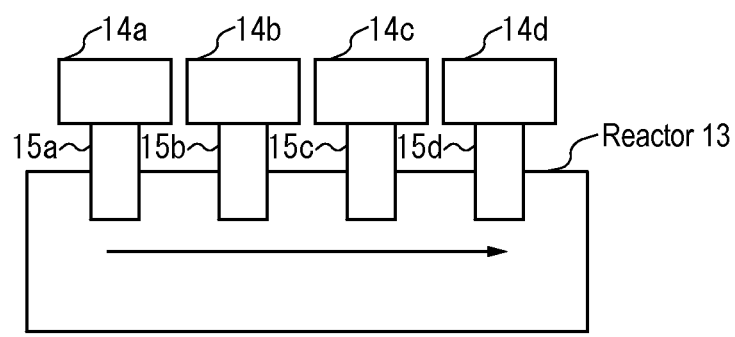
FIG. 7B is a view illustrating positions for microwave irradiation according to the example.

Furthermore, in this example, the chemical reaction apparatus 1 may be provided with two or more microwave generators 14, and the two or more microwave generators 14 may generate microwaves having two or more frequencies. That is to say, the content of the reactor 13 may be irradiated with microwaves having two or more frequencies. In that case, the microwaves having two or more frequencies may be irradiated on the same position, or may be respectively irradiated on different positions. For example, as shown in FIG. 7A, microwaves having frequencies X and Y respectively generated by microwave generators 14a and 14d may be irradiated on the same position in the reactor 13, that is, at the midstream in the reactor 13. Note that the microwaves having the frequencies X and Y are respectively transmitted via waveguides 15a and 15d to the reactor 13. Furthermore, for example, as shown in FIG. 7B, microwaves having a frequency X generated by microwave generators 14a, 14b, and 14c may be irradiated on the side from the upstream to the midstream in the reactor 13, and microwaves having a frequency Y generated by a microwave generator 14d may be irradiated on the downstream side in the reactor 13. Note that the microwaves having the frequency X are respectively transmitted via waveguides 15a, 15b, and 15c to the reactor 13. Furthermore, the microwaves having the frequency Y are transmitted via a waveguide 15d to the reactor 13. FIGS. 7A and 7B are both views of the reactor 13 from above, wherein the arrows in the drawings indicate the flow of the content inside the reactor 13. If microwaves having two or more frequencies are irradiated, the number of frequencies may be two, or three or more. There is no limitation on the combination of two or more frequencies, as long as they are selected from the range from 300 MHz to 300 GHz. For example, if microwaves having two frequencies are irradiated, examples of the combination of these frequencies include 2.45 GHz and 5.8 GHz, 2.45 GHz and 24 GHz, 2.45 GHz and 913 MHz, 5.8 GHz and 24 GHz, 5.8 GHz and 913 MHz, and 24 GHz and 913 MHz. Furthermore, if microwaves having two or more frequencies are irradiated, there is no limitation on the irradiation timing. For example, microwaves having two or more frequencies may be simultaneously irradiated, or may be irradiated such that the frequencies respectively correspond to different irradiation periods. For example, in the latter case, microwaves having the frequency X may be irradiated in one period, and microwaves having the frequency Y may be irradiated in the next period. Note that if microwaves having two or more frequencies are irradiated, a material that is not affected by the action (e.g., heating, etc.) of microwaves having one frequency can be also affected, and, thus, a wider range of materials can be affected by the microwaves.

Furthermore, in the foregoing example, information such as a threshold value, a numerical expression, or an address used in each constituent element in the processing and the like may be retained in a storage medium (not shown) temporarily or for a long period of time even if not specified in the description above. Furthermore, information may be accumulated in the storage medium (not shown) by each constituent element or an accumulating portion (not shown). Furthermore, information may be read from the storage medium (not shown) by each constituent element or a reading portion (not shown).

Furthermore, in the foregoing example, if information used in each constituent element or the like, for example, information such as a threshold value, an address, or various setting values used in each constituent element in the processing may be changed by a user, the user may change such information as appropriate even if not specified in the description above, but there is no limitation to this. If the user may change such information, the change may be realized by, for example, an accepting portion (not shown) that accepts a change instruction from the user and a changing portion (not shown) that changes information according to the change instruction. The change instruction may be accepted by the accepting portion (not shown), for example, by accepting information from an input device, by receiving information transmitted via a communication line, or by accepting information read from a predetermined storage medium.

Furthermore, in the foregoing example, each constituent element may be configured by dedicated hardware, or, alternatively, constituent elements that can be realized as software may be realized by executing a program. For example, each constituent element may be realized by a program execution portion such as a CPU reading and executing a software program stored in a storage medium such as a hard disk or a semiconductor memory.

Furthermore, it will be appreciated that the present invention is not limited to the example set forth herein, and various modifications are possible within the scope of the present invention.

As described above, the chemical reaction apparatus and the like according to the present invention are effective in that the raw material and the like can be efficiently irradiated with microwaves, and, thus, they are useful, for example, as a chemical reaction apparatus and the like for causing a chemical reaction in which heating is necessary.

The invention claimed is:

1. A chemical reaction apparatus, comprising:
   a horizontal flow reactor configured to flow a content horizontally, comprising:
      an upstream side with an inlet configured to receive unreacted raw material;
      a downstream side with an outlet to discharge a reacted produced material;
   a plurality of chambers continuously arranged in series between the upstream side and the downstream side;
   a plurality of partition plates, partitioning the inside of the reactor into the plurality of chambers, comprise a recess portion on an upper side of the partition plates;
   a flow path, provided through the recess portion in the plurality of partition plates, through which the content flows from the upstream side to the downstream side; and
   an unfilled space provided above the horizontal flow reactor continuous above the upstream side to the downstream side and continuous above the plurality of partition plates in the reactor;
   a plurality of microwave generators configured to generate microwaves;
   a plurality of waveguides configured to transmit the microwaves generated by the plurality of microwave generators to the unfilled space in the reactor, respectively;
   at least one thermometer configured to measure a temperature inside the reactor;
   a microwave generator controller configured to control the plurality of microwave generators according to the temperature measured by the at least one thermometer; and
   an agitation unit comprising a rotation member configured to agitate the content inside the reactor using rotating agitation and the rotation member reflects microwaves to assist in the heating in the unreacted raw material.

2. The chemical reaction apparatus according to claim 1, wherein the reactor is configured to allow a raw material and a solid catalyst to flow therein, and
   the chemical reaction apparatus further comprises a catalyst separating portion configured to separate the solid catalyst from a product material after a reaction in the reactor.

3. The chemical reaction apparatus according to claim 2, wherein the solid catalyst is microwave-absorbing or microwave-sensitive.

4. The chemical reaction apparatus according to claim 1, wherein the flow path allows the content to flow through a void in each of the partition plates.

5. The chemical reaction apparatus according to claim 1, wherein the partition plates each transmit microwaves.

6. The chemical reaction apparatus according to claim 1, wherein the plurality of microwave generators generate microwaves having at least two frequencies.

7. The chemical reaction apparatus according to claim 1, wherein the at least one thermometer comprises multiple thermometers disposed in the reactor, measuring the temperature inside at least two chambers in the reactor; and
   wherein the microwave generator controller is configured to control each of the microwave generators to maintain at least one of a uniform predetermined temperature or a predetermined temperature range over all chambers inside the reactor according to an average of the temperatures measured by two or more thermometers of the multiple thermometers.

8. The chemical reaction apparatus according to claim 1, wherein the flow path allows the content to flow over each of the plurality of partition plates, and
   wherein one of the plurality of partition plates is located under a transmission end of at least one of the plurality of waveguides.

9. The chemical reaction apparatus according to claim 1, wherein the plurality of partition plates have voids in themselves, and the chemical reaction apparatus further comprises a flow path, provided through the voids in the plurality of partition plates, through which the content flows from the upstream side to the downstream side.

10. The chemical reaction apparatus according to claim 9, wherein the agitation unit creates a second flow path by which a portion of the content flows from the downstream side to upstream side through the voids.

11. The chemical reaction apparatus according to claim 1, further comprising a cooler, downstream of the outlet, configured to lower a temperature of the reacted produced material.

12. A chemical reaction apparatus, comprising:
    a horizontal flow reactor configured to flow a content horizontally, comprising:
       an upstream side with an inlet configured to receive unreacted raw material;
       a downstream side with an outlet to discharge a reacted produced material;
    a plurality of chambers continuously arranged in series between the upstream side and the downstream side;
    a plurality of partition plates partitioning the inside of the reactor into the plurality of chambers;
    a flow path, provided in the plurality of partition plates, through which the content flows from the upstream side to the downstream side; and an unfilled space provided above the horizontal flow reactor continuous above the upstream side to the downstream side and continuous above the plurality of partition plates in the reactor;
a plurality of microwave generators configured to generate microwaves;
a plurality of waveguides configured to transmit the microwaves generated by the plurality of microwave generators to the unfilled space in the reactor, respectively;
at least one thermometer configured to measure a temperature inside the reactor;
a microwave generator controller configured to control the plurality of microwave generators according to the temperature measured by the at least one thermometer;
a mixing portion configured to mix a raw material and a solid catalyst into the unreacted raw material; and
an agitation unit comprising a rotation member configured to agitate the content inside the reactor using rotating agitation and the rotation member reflects microwaves to assist in the heating in the unreacted raw material,
wherein the unreacted raw material mixed by the mixing portion is loaded into the inlet at the upstream side in the reactor, and
wherein the mixing portion is separate from the horizontal flow reactor.

13. The chemical reaction apparatus according to claim 12, wherein the solid catalyst is microwave-absorbing or microwave-sensitive.

14. The chemical reaction apparatus according to claim 12, wherein the mixing portion mixes at least a raw material by rotating at least one of a blade-like member, a wing-like member, and a screw-like member.

15. The chemical reaction apparatus according to claim 12, wherein the raw material and the solid catalyst are mixed in the mixing portion separate from the plurality of waveguides.

16. The chemical reaction apparatus according to claim 12, wherein the plurality of partition plates have voids in themselves, and the flow path is provided through the voids in the plurality of partition plates.

17. The chemical reaction apparatus according to claim 16, wherein the agitation unit creates a second flow path by which a portion of the content flows from the downstream side to upstream side through the voids.

18. The chemical reaction apparatus according to claim 12, further comprising a cooler, downstream of the outlet, configured to lower a temperature of the reacted produced material.

19. A chemical reaction apparatus, comprising:
a horizontal flow reactor configured to flow a content horizontally, comprising:
an upstream side with an inlet configured to receive unreacted raw material;
a downstream side with an outlet to discharge a reacted produced material;
a plurality of chambers continuously arranged in series between the upstream side and the downstream side;
a plurality of partition plates partitioning the inside of the reactor into the plurality of chambers;
a flow path, provided in the plurality of partition plates, through which the content flows from the upstream side to the downstream side; and
an unfilled space provided above the horizontal flow reactor continuous above the upstream side to the downstream side and continuous above the plurality of partition plates in the reactor;
a plurality of microwave generators configured to generate microwaves;
a plurality of waveguides configured to transmit the microwaves generated by the plurality of microwave generators to the unfilled space in the reactor, respectively;
at least one thermometer configured to measure a temperature inside the reactor;
a microwave generator controller configured to control the plurality of microwave generators according to the temperature measured by the at least one thermometer;
a mixing portion configured to mix an unheated raw material; and
an agitation unit comprising a rotation member configured to agitate the content inside the reactor using rotating agitation and the rotation member reflects microwaves to assist in the heating in the unreacted raw material,
wherein the unheated raw material mixed by the mixing portion is loaded into the inlet at the upstream side in the reactor, and
wherein the mixing portion is separate from the horizontal flow reactor.

20. The chemical reaction apparatus according to claim 19, wherein the mixing portion mixes at least a raw material by rotating at least one of a blade-like member, a wing-like member, and a screw-like member.

21. The chemical reaction apparatus according to claim 19, wherein the raw material is mixed in the mixing portion separate from the plurality of waveguides.

22. The chemical reaction apparatus according to claim 19, wherein the plurality of partition plates have voids in themselves, and the flow path is provided through the voids in the plurality of partition plates.

23. The chemical reaction apparatus according to claim 22, wherein the agitation unit creates a second flow path by which a portion of the content flows from the downstream side to upstream side through the voids.

24. The chemical reaction apparatus according to claim 19, further comprising a cooler, downstream of the outlet, configured to lower a temperature of the reacted produced material.

25. A chemical reaction apparatus, comprising:
a horizontal flow reactor configured to flow a content horizontally with an unfilled space being provided thereabove, comprising:
an upstream side with an inlet configured to receive unreacted material;
a downstream side with an outlet to discharge a reacted produced material;
a microwave generator configured to generate microwaves; and
at least one waveguide configured to transmit the microwaves generated by the microwave generator to the unfilled space in the reactor,
wherein the reactor has multiple partition plates that partition the inside of the reactor into multiple chambers that are continuously arranged in series, and
the partition plates are provided with a flow path through which the content flows from the upstream side to the downstream side,
wherein the flow path is a flow path that allows the content to flow over each of the partition plates.

* * * * *